(12) United States Patent
Hodson et al.

(10) Patent No.: US 8,985,102 B2
(45) Date of Patent: Mar. 24, 2015

(54) DRY POWDER INHALERS

(75) Inventors: Peter D. Hodson, Bracknell (GB);
Stephen W. Stein, Saint Paul, MN (US);
Herbert C. Chiou, Saint Paul, MN (US);
Zhaolin Wang, Saint Paul, MN (US);
Thomas S. Robison, Saint Paul, MN (US);
Michael K. Domroese, Saint Paul, MN (US);
Blake D. Walburg, Saint Paul, MN (US)

(73) Assignee: Adamis Pharmaceuticals Corporation, San Diego, CA (US)

( * ) Notice: Subject to any disclaimer, the term of this patent is extended or adjusted under 35 U.S.C. 154(b) by 608 days.

(21) Appl. No.: 13/320,762

(22) PCT Filed: May 18, 2010

(86) PCT No.: PCT/US2010/035280
§ 371 (c)(1),
(2), (4) Date: Jan. 13, 2012

(87) PCT Pub. No.: WO2010/135340
PCT Pub. Date: Nov. 25, 2010

(65) Prior Publication Data
US 2012/0132203 A1 May 31, 2012

Related U.S. Application Data

(60) Provisional application No. 61/179,220, filed on May 18, 2009.

(51) Int. Cl.
A61M 15/00 (2006.01)
(52) U.S. Cl.
CPC ....... *A61M 15/0045* (2013.01); *A61M 15/0065* (2013.01); *A61M 15/0008* (2014.02); *A61M 15/0026* (2014.02); *A61M 15/0043* (2014.02); *A61M 15/0051* (2014.02); *A61M 15/0055* (2014.02); *A61M 15/0091* (2013.01); *A61M 2202/064* (2013.01)
USPC ................................ 128/203.15; 128/203.12
(58) Field of Classification Search
USPC ............. 128/200.24, 203.12, 203.15, 203.21
See application file for complete search history.

(56) References Cited

U.S. PATENT DOCUMENTS 3,704,816 A * 12/1972 Gandrud ....................... 222/368
5,161,524 A 11/1992 Evans
(Continued)

FOREIGN PATENT DOCUMENTS

EP 0 451 745 10/1991
EP 0 520 440 12/1992
(Continued)

OTHER PUBLICATIONS

Ayton, F.; "Chapter 7—Plastics as barrier materials in beverage packaging"; Handbook of Beverage Packaging; Edited by G. A. Giles; Blackwell Publishing;1999; pp. 120-138.
(Continued)

*Primary Examiner* — Annette Dixon
(74) *Attorney, Agent, or Firm* — K&L Gates LLP; Louis C. Cullman; Robert W. Winn

(57) ABSTRACT

Dry powder inhalers and dry powder inhaler storage cassettes including a compartment housing an elongate carrier preloaded with a plurality of doses of finely divided powder.

20 Claims, 7 Drawing Sheets

(56) References Cited

U.S. PATENT DOCUMENTS

| | | | |
|---|---|---|---|
| 5,192,548 A | 3/1993 | Velasquez et al. | |
| 5,295,479 A | 3/1994 | Lankinen | |
| 5,388,572 A | 2/1995 | Mulhauser et al. | |
| 5,408,994 A | 4/1995 | Wass et al. | |
| 5,619,984 A | 4/1997 | Hodson et al. | |
| 5,657,748 A | 8/1997 | Braithwaite | |
| 5,724,960 A | 3/1998 | Bruna | |
| 5,740,793 A * | 4/1998 | Hodson et al. | 128/203.15 |
| 6,012,454 A | 1/2000 | Hodson et al. | |
| 6,065,472 A | 5/2000 | Anderson et al. | |
| 6,536,427 B2 | 3/2003 | Davies et al. | |
| 6,696,157 B1 | 2/2004 | David et al. | |
| 6,698,425 B1 | 3/2004 | Widerström | |
| 8,127,763 B2 * | 3/2012 | Smyth et al. | 128/203.15 |
| 2006/0081246 A1 | 4/2006 | Goede et al. | |
| 2007/0209661 A1 * | 9/2007 | Smyth et al. | 128/203.12 |

FOREIGN PATENT DOCUMENTS

| | | |
|---|---|---|
| GB | 2 242 134 | 9/1991 |
| WO | WO 92/05824 | 4/1992 |
| WO | WO 92/18188 | 10/1992 |
| WO | WO 94/12230 | 6/1994 |
| WO | WO 96/08284 | 3/1996 |
| WO | WO 98/26828 | 6/1998 |
| WO | WO 98/41255 | 9/1998 |
| WO | WO 99/44663 | 9/1999 |
| WO | WO 00/53248 | 9/2000 |
| WO | WO 00/74754 | 12/2000 |
| WO | WO 01/21238 | 3/2001 |
| WO | WO 02/11800 | 2/2002 |
| WO | WO 2007/018568 | 2/2007 |
| WO | WO 2007/112267 | 10/2007 |

OTHER PUBLICATIONS

D. Ganderton et al.; "Drug Delivery to the Respiratory Tract"; Chapter 9—The formulation and evaluation of pressurised metered-dose inhalers; published by Ellis Horwood, Chichester; 1987; pp. 87-118.

Brochure from TOPAS® Advanced Polymers Cyclic Olefin Copolymer (COC) entitled Packaging; 31 pgs (date unknown but believed to be prior to the date of the fiing of the present application).

\* cited by examiner

DRY POWDER INHALERS

CROSS-REFERENCE TO RELATED APPLICATIONS

This application is a national phase entry of International Application No. PCT/US2010/035280, filed May 18, 2010, which claims priority to U.S. Provisional Application No. 61/179,220 filed May 18, 2009, each of which is incorporated by reference in their entireties.

FIELD

This invention relates to dry powder inhalers as well as to cassettes, such as removable and/or re-fill supply cassettes, for use in dry powder inhalers.

BACKGROUND

Asthma and other respiratory diseases have long been treated by the inhalation of appropriate medicaments. For many years the two most widely used and convenient choices of treatment have been the inhalation of medicament from a drug solution or suspension in a pressurised metered dose inhaler (pMDI), or inhalation of powdered drug, generally admixed with an excipient, from a dry powder inhaler (DPI). Following strong concern about the link between depletion of the earth's ozone layer and chlorofluorocarbon (CFC) emissions, the use of these materials in pressurised inhalers is being phased out and interest in DPI systems has been stimulated.

Quite a number of DPI systems or components for DPI systems have been described including those described in, for example, GB 2242134 (Davies et al.), U.S. Pat. No. 5,192,548 (Velasquez et al.), U.S. Pat. No. 5,619,984 (Hodson et al.), U.S. Pat. No. 5,657,748 (Braithwaite), WO 98/41255 (Jennings et al.), WO 01/21238 (Seppala), and US 2006/0081246 (Goede et al.).

In practice most DPIs use either bulk powder reservoirs or individual pre-measured doses sealed within individual containers in the form of capsules or blisters, such as blister packs and blister strips.

There are, however, problems associated with accurately metering a measured small quantity (e.g., 500 micrograms or less) of powder from a bulk reservoir within an inhaler. With many drugs, e.g., potent drugs, this introduces the necessity to add excipients, such as lactose powder, to significantly increase the quantity of powder to be metered. Such excipients are however generally undesirable as they can pose subsequent powder deagglomeration problems and can cause dryness and other unwanted effects in the patient's mouth.

Furthermore, ingress of moisture (ambient moisture and/or moisture from a patient's breath e.g., inadvertently exhaled into the inhaler) into e.g., the bulk powder reservoir can pose a serious problem. Many biologically active substances, such as medicaments, delivered by inhalation are susceptible to physical or chemical change and/or degradation in the presence of moisture vapor. For example, the powdered particles may re-crystallize in the presence of adsorbed moisture vapor, which may lead to an effective increase in the median particle size of the powdered material, which in turn may lead to reduced penetration of the particles into relevant delivery sites in the lung, e.g., the lower airway passages in the lung.

DPIs where the powder supply, e.g., powdered medicament, is provided in the form of capsules or blisters generally have somewhat better moisture protection, due to the fact that each individual dose is sealed off, where typically a dose on a carrier component is covered and sealed with a lid component. The manufacturing of such capsules, blister packs or blister strips, including accurately metered, small quantities of powder per capsule/blister for use in a DPI, can be difficult and/or quite expensive. Furthermore, DPIs using such a powder supply normally require complex mechanisms for opening the individually sealed capsules or blisters (e.g., mechanisms for peeling the lid off, puncturing the capsule/blister, etc.).

SUMMARY

According to one aspect of the present invention there is provided a dry powder inhalation device comprising: a chamber; a patient port in communication with said chamber; a compartment housing an elongate carrier preloaded with a plurality of doses of finely divided powder comprising a biologically active substance, said powder being releasably retained on a surface of the carrier, said compartment being configured such that said preloaded doses are sealed within said compartment and such that the carrier may be advanced from the compartment to the chamber through an exit provided with a moisture barrier sealing system; an advancement mechanism for advancing a portion of the carrier from the compartment to within the chamber so that the powder associated with an advanced area of the carrier can be released from the carrier for inhalation by the patient through the patient port; wherein the moisture barrier sealing system is configured and arranged such that it is relaxable during advancement of the carrier, said sealing system being in sealing configuration prior to an advancement of the carrier, relaxed upon an advancement of the carrier and returned to its sealing configuration at the latest after release of the powder associated with said area of the carrier.

Such a dry powder inhalation device is advantageous in that it provides effective protection against moisture and moisture ingress, while at the same time allowing the provision of a carrier preloaded with finely divided powder to provide a plurality of doses, without the necessity of having to provide individual doses and to hermetically seal each of these individual doses. In other words the finely divided powder does not need to be pre-metered into doses and the carrier need not be covered and sealed with a lid component, such as a foil lid layer component, since the moisture barrier sealing system advantageously returns to its sealing configuration at the latest after release of the powder associated with the advanced area of the carrier prior to advancement of the next portion of the carrier.

Protection against moisture and moisture ingress can be further facilitated in certain favorable embodiments in which the moisture barrier sealing system is configured and arranged such that the sealing system is returned to its sealing configuration at least prior to release of the powder associated with said area of the carrier. Protection against moisture and moisture ingress can be yet further enhanced in certain particularly favorable embodiments in which the moisture barrier sealing system is configured and arranged such that the sealing system is returned to its sealing configuration upon cessation of advancement of the carrier. The latter mentioned embodiments are particularly advantageous in that the moisture barrier sealing system may generally and advantageously work in a "dead man's handle" manner wherein a seal is applied to the supply compartment exit whenever the carrier is not being advanced, i.e. the moisture barrier sealing system generally operates such that it returns automatically to its sealing configuration as soon as advancement of the carrier stops. (Under the phrases such as "sealing system returns" or "sealing system is returned" as used herein it will be understood that the sealing system may return on its own accord or through the action of a separate mechanism/element.)

The compartment may be favorably provided within a cassette that is reversibly removable from the dry powder inhaler. Such a cassette can be in itself advantageous in that it can be used as a powder storage and/or supply unit, e.g., an original supply unit and/or a re-fill supply unit, for a dry powder inhaler.

According to a second aspect of the present invention there is provided a device for storing dry powder for use in a dry powder inhaler, said device provided in the form of a cassette comprising: a compartment housing an elongate carrier preloaded with a plurality of doses of finely divided powder comprising a biologically active substance, said powder being releasably retained on a surface of the carrier; said compartment being configured such that preloaded doses are sealed within said compartment and such that the carrier may be advanced from the compartment to the outside of the compartment through an exit provided with a moisture barrier sealing system, wherein said device is configured and arranged such that during use in a dry powder inhaler wherein a portion of the carrier is advanced so that the powder associated with an advanced area can be released from the carrier for inhalation by the patient through the patient port of the inhaler, the moisture barrier sealing system is relaxable during advancement of the carrier, so that said sealing system is in sealing configuration prior to an advancement of the carrier, will relax upon an advancement of the carrier and will be returned to its sealing configuration at the latest after release of the powder associated with said area of carrier.

In certain favorable embodiments of devices in accordance with aspects described above it has been found particularly advantageous to have the area of the carrier, which has been advanced into the chamber so that the powder associated with said area of the carrier can be released from the carrier for inhalation by the patient through the patient port (referred to in the following simply as the "dose-release area") be clamped at its "ends" during release of the powder associated with said area of the carrier. This double-clamping has been found to be advantageous in reducing and/or preventing powder from other areas of the carrier, either behind or ahead of the dose-release area within the chamber, from being dislodged from the carrier when the powder in the dose-release area is released, and thus minimizing and/or preventing build-up of stray powder within the inhaler and correspondingly allowing for improved reproducibility of the emitted dose. Accordingly in certain embodiments, devices may favorably further comprise a first clamping system and a second clamping system, wherein the systems are configured and arranged such that they are moved into a clamping configuration at least prior to release of the powder associated with the dose-release area, so that the dose-release area will be clamped between the first and the second clamping systems during release of the powder associated with the dose-release area. In other words the dose-release area is positioned between two clamping systems and clamped by the two systems prior to release of the powder. In other embodiments, e.g., where the moisture barrier sealing system is arranged and configured to return to its sealing configuration at least prior to release of the powder associated with the dose-release area, the moisture barrier sealing system may favorably also act as a clamping system. Such embodiments may thus favorably include a clamping system in addition to the moisture barrier sealing system, said clamping system being configured and arranged such that it is moved into a clamping configuration at least prior to release of the powder associated with the dose-release area and wherein said clamping system and said moisture barrier sealing system are configured and arranged relative to one another such that said area of the carrier will be clamped between the clamping system and the moisture barrier sealing system during release of the powder associated with the dose-release area. In other words the dose-release area is positioned between the moisture barrier sealing system and a second clamping system and clamped by the two systems prior to release of the powder associated with the dose-release area.

A double-clamping can also be advantageously used in dry powder inhalers which do not make use of a moisture-barrier sealing system in accordance with the aforementioned first and second aspects. Accordingly there is provided in a third aspect of the present invention a dry powder inhalation device comprising: a chamber; a patient port in communication with said chamber; an elongate carrier preloaded with a plurality of doses of finely divided powder comprising a biologically active substance, said powder being releasably retained on a surface of the carrier; an advancement mechanism for advancing a portion of the carrier to within the chamber so that the powder associated with an advanced area of the carrier can be released from the carrier for inhalation by the patient through the patient port; and a first clamping system and a second clamping system, wherein the first and second clamping systems are configured and arranged such that they are moved into a clamping configuration at least prior to release of the powder associated with said area of the carrier, so that said area of the carrier will be clamped between the first and the second clamping systems during release of the powder associated with said area of the carrier.

Devices in accordance with the second aspect described herein, e.g., cassettes, for storing powder for use in a dry powder inhaler may also comprise an appropriate clamping system or clamping systems.

Clamping systems may also be provided in storage devices that do not include a moisture-barrier sealing system in accordance with the aforementioned first and second aspects. Thus in a fourth aspect of the present invention there is provided a device for storing dry powder for use in a dry powder inhaler, said device comprising: an elongate carrier preloaded with a plurality of doses of finely divided powder comprising a biologically active substance, said powder being releasably retained on a surface of the carrier; a first clamping system and a second clamping system, wherein said device is configured and arranged such that during use in a dry powder inhaler wherein a portion of the carrier is advanced so that the powder associated with an advanced area can be released from the carrier for inhalation by the patient through the patient port of the inhaler, the first and second clamping systems will be moved into a clamping configuration at least prior to release of the powder associated with said area of the carrier, so that said area of the carrier will be clamped between the first and the second clamping systems during release of the powder associated with said area of the carrier.

Dependent claims define further embodiments of the invention.

BRIEF DESCRIPTION OF DRAWINGS

The invention will now be described with reference to the accompanying drawings in which:

FIGS. 1 to 3 represent partial cross sectional illustrations of an exemplary dry powder inhaler in its closed position, a partially open position and its fully opened position, respectively.

FIGS. 4 to 7 represent cross sectional illustrations of a particular region of the exemplary dry powder inhaler in its closed position, a partially open position and its fully opened position, as well as at actuation, respectively.

DETAILED DESCRIPTION

It is to be understood that the present invention covers all combinations of particular, suitable, desirable, favorable, advantageous and preferred aspects of the invention described herein.

Figure 1:
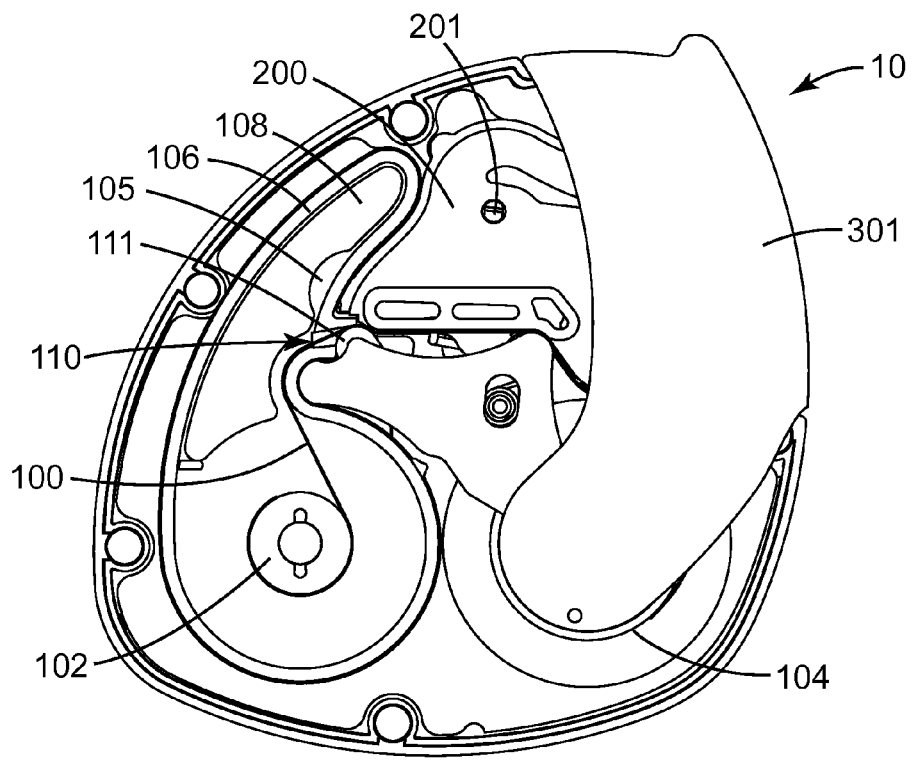
Figure 2:
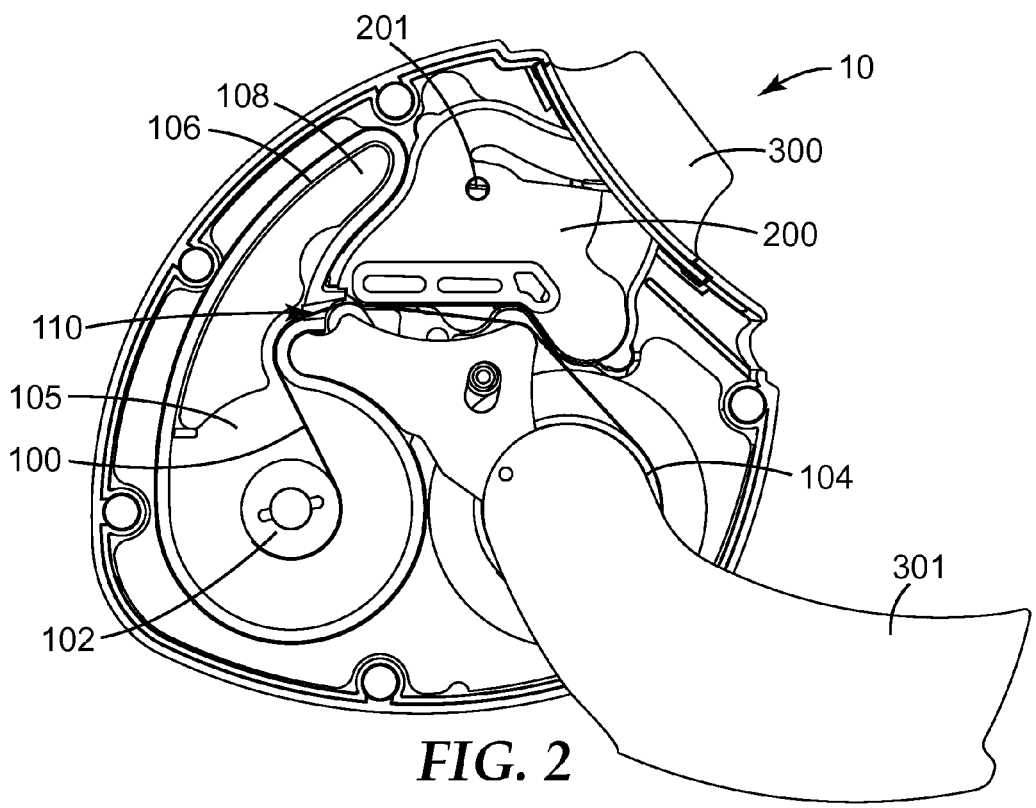
Figure 3:
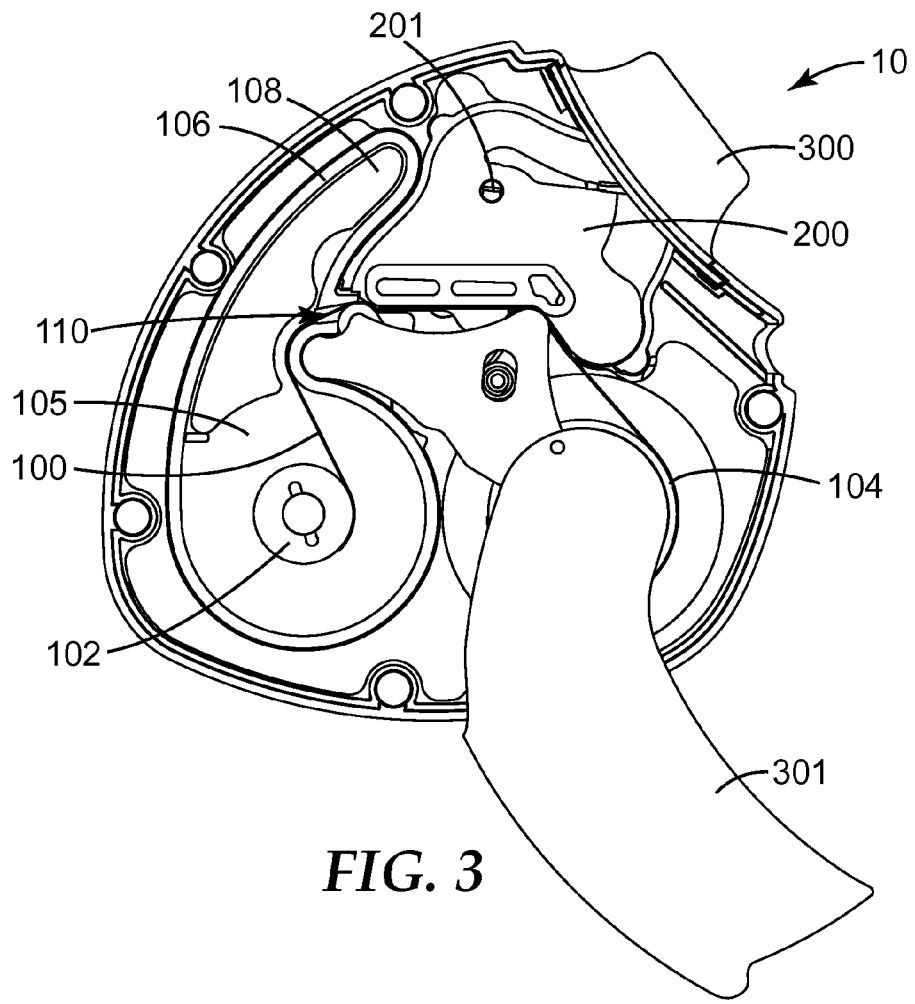

FIGS. 1 to 3 represent partial cross sectional illustrations of an exemplary dry powder inhaler (10) in its closed position, a partially open position and its fully opened position, respectively. The inhaler (10) includes a chamber (200) and a patient port, in particular in the form of a mouthpiece (300), in communication with said chamber. The patient port is not visible in FIG. 1, because in the closed position of the illustrated inhaler the mouthpiece is covered by a cover (301). Only when the user opens the inhaler for use, i.e. opens the mouthpiece-cover (301) as shown in FIGS. 2 and 3, does the patient port (300) become visible. The inhaler (10) also includes an elongate carrier (100) preloaded with finely divided powder comprising a biologically active substance (not visible).

The elongate carrier can be provided in a variety of forms, such as a tape, web, belt or cord. Desirably the carrier is provided in the form of a tape or a web. The elongate carrier may have any ratio of length to width but said ratio is generally greater than 5 to 1, usually greater than 10 to 1, more particularly from about 100:1 to about 1000:1. The elongate carrier may typically have a width of 5 mm to 20 mm, e.g., 10 mm. Its thickness may typically be from 75 microns to 500 microns, particularly from 100 microns to 250 microns, more particularly from about 120 microns to 175 microns. If desired, the elongate carrier may be provided with a lid component, for example to cover and/or seal off individual doses. However, such covering and sealing is generally not needed in embodiments in accordance with certain aspects of the invention described herein, and thus accordingly favorably the carrier does not comprise a lid component covering and sealing off individual doses.

The powder comprising a biologically active substance, typically a medicament, is releasably retained on a surface of the carrier. The powder may be retained on the carrier by attraction forces, such as electrostatic attraction, van der Waals forces, physical attraction; mechanical binding; and/or wedging. Alternatively powder may be retained on the carrier by covering the powder using a lid component; however as indicated supra it is not desirable (nor necessary in accordance with certain aspects of the invention described herein) to use a lid component. To facilitate favorable release characteristics, it is desirable not to retain the powder on the carrier via adhesives or glues. The aforesaid expression "mechanical binding" generally refers to powder particles being held onto the carrier by intrinsic mechanical means of the carrier material, e.g., within the entanglement of fibers of a nonwoven web. The expression "wedging" generally refers to loading powder particles within/into particular structures of the elongate carrier (e.g., micro-depressions provided in a plastic elongate carrier or porous spaces of a nonwoven elongate carrier). One or more surfaces of the carrier and optionally the interior of the carrier may be configured to assist in retaining the particles of powder.

A carrier may be constructed from one or more of a wide range of natural and synthetic materials e.g., polyethylene, polypropylene, polyester e.g., polyethylene terephthalate, polytetrafluoroethylene or a co-polymer thereof, ethylene vinyl alcohol, or cellulose. The materials may be in the form of non-woven fibrous materials, loose weave materials or fabrics, materials having a surface pile, films, microporous materials, microgrooved materials, cords of twisted fibers, or any other suitable material or composites of more than one material. Desirably a carrier is constructed of a material or a material composite where small surface depressions, dimples, grooves, recesses, interstices, apertures or embossed surface structures having a typical size of equal to or less than 500 microns in either depth or height and of greater than 0.1 microns in at least one other dimension are provided to help to retain the particles of powder. Various materials for carriers as well as particular forms of carriers suitable for use herein are disclosed in U.S. Pat. No. 5,619,984 (Hodson et al.), the contents of said patent in its entirety being incorporated herein by reference.

The form of the elongate carrier can in part play a role in the storage format. For example a cord may be conveniently stored as a coil or wound on a spool, while a tape or web may be for example folded or wound on a spool. Generally it is favorable for an elongate carrier to be wound on a spool.

As shown in the exemplary embodiment illustrated in FIGS. 1 to 3, the carrier (100) may be stored initially on a supply spool (102) and advanced onto an uptake spool (104) during use of the inhaler. During use of an inhaler, in general, a portion of the carrier is advanced to within the chamber so that the powder associated with an advanced area of the carrier can be and is, upon actuation, released from the carrier for inhalation by the patient through the patient port.

For ease of illustration, as well as of viewing, a total length of carrier shorter than typical has been shown in FIGS. 1 to 3. The carrier (100), with its preloaded finely divided powder providing a plurality of doses, is housed within a compartment (105), with the compartment being configured so that the preloaded doses are sealed within the compartment and such that the carrier may be advanced from the compartment to the chamber (200) through an exit (not quite visible in FIGS. 1 to 3) provided with a moisture barrier sealing system (110).

Figure 4:
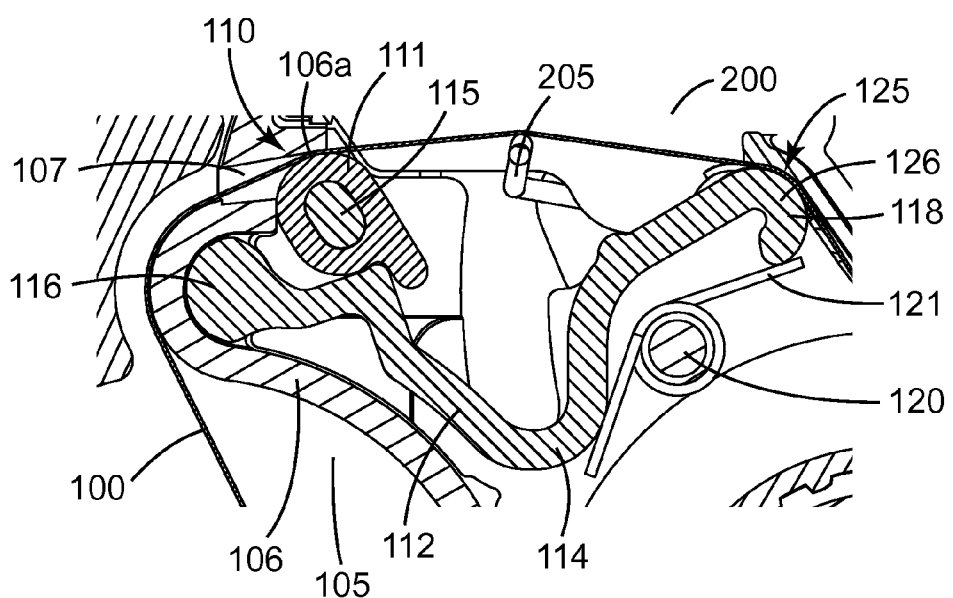
Figure 5:
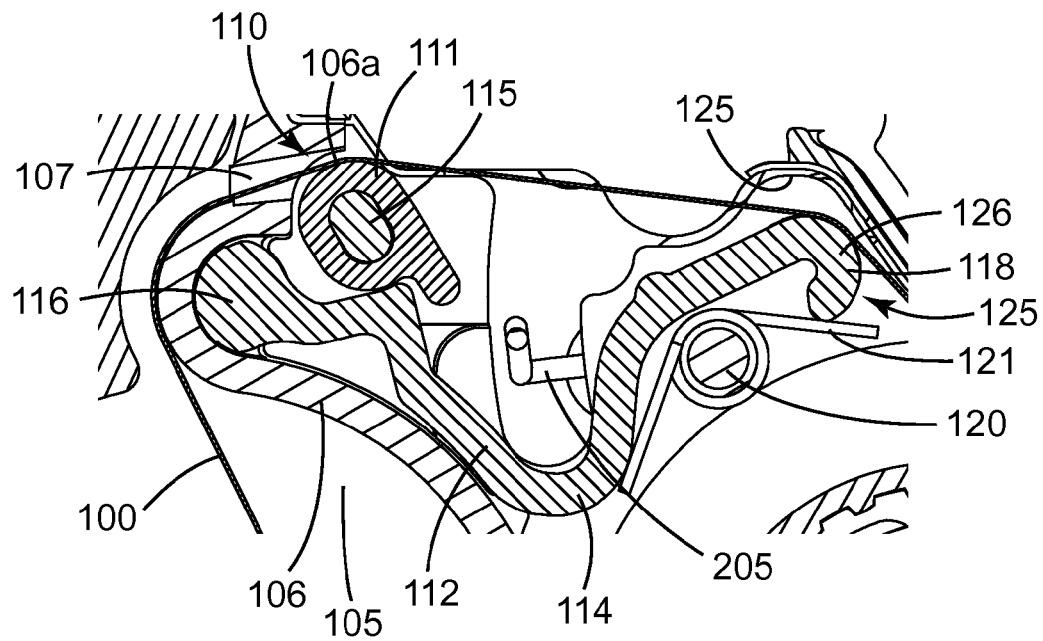
Figure 6:
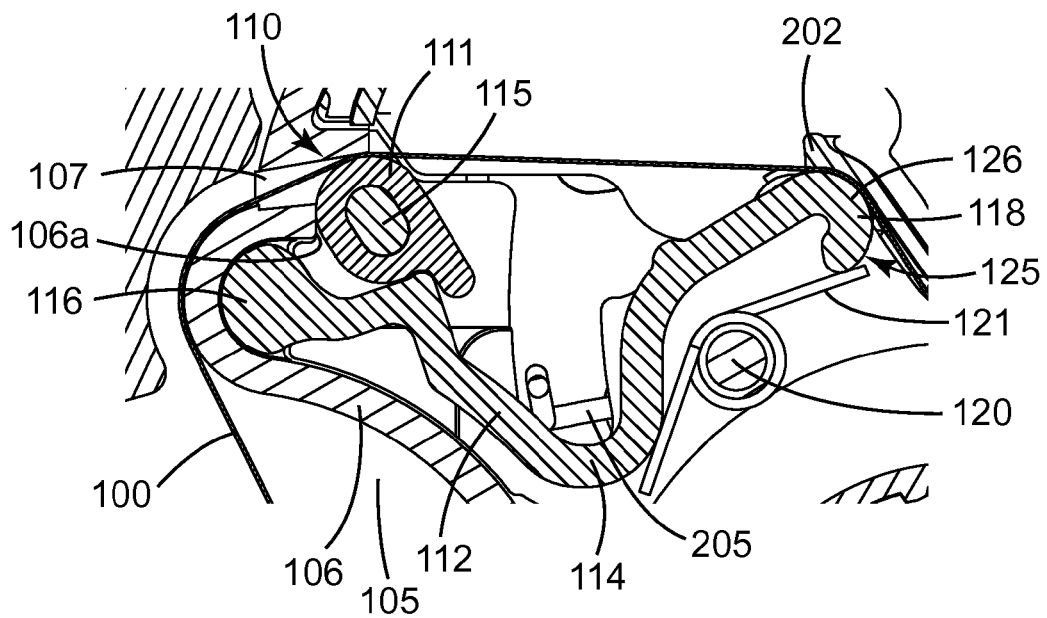

This may be better appreciated in FIGS. 4 to 6, which show a cross-sectional, detailed view of the region about the compartment exit and the lower portion of the chamber of the exemplary inhaler, at positions with the mouthpiece cover closed (prior to an advancement), partially open (during advancement) and fully open (prior to powder release) respectively. In the Figures the compartment (105) is to the left, and the compartment wall (106) is provided with an exit (107), best seen in FIG. 5, through which the carrier (100) is advanced. In the closed position shown in FIG. 4, it can be seen that the moisture barrier sealing system (110) is in a sealing configuration; in particular a seal (111) is pushing against the carrier and the outer surface (106a) of the compartment wall (106), thereby sealing over the exit (107) of the compartment. As shown in FIG. 5—showing a partially open position—as the user opens the mouthpiece cover, the sealing system relaxes allowing the seal (111) to disengage from the compartment outer wall surface (106a) and the carrier (100) to advance (discussed in more detail infra). When the user has fully opened the cover, or better said, when advancement of the carrier has been completed by the user, and prior to release of powder associated with said advanced area of the carrier, the sealing system returns to its sealing configuration where, as can be seen in FIG. 6, the seal (111) is once again clamped against the carrier (100) and the outer surface (106a) of the wall (106) of the compartment (105), thereby sealing over the exit (107) of the compartment.

In favorable embodiments the moisture barrier sealing system is configured and arranged such that the sealing system is returned to its sealing configuration at least prior to release of the powder associated with the dose-release area of the carrier.

The moisture barrier sealing system suitably comprises a seal or seals. The seal(s) typically is that component of the system which seals over the exit of the compartment when the system is in its sealing configuration. Suitable materials for a moisture barrier seal may have a Shore A hardness value equal to or less than 75, in particular equal to or less than 65 (as determined by ASTM test number D2249). Suitable materials for a moisture barrier seal may have a Shore A hardness value equal to or greater than 35, in particular equal to or greater than 45 (as determined by ASTM test number D2249). Favorably such a seal is resilient, and thus most desirably comprises an elastomeric material, such as Silicone rubber. Preferably a thermoplastic elastomer is used, e.g., EPDM and polypropylene blends, such as those available under the trade designation SANTOPRENE, or styrene-isoprene copolymers, such as those available under the trade designation KRATON. Such elastomers may be co-molded with another component of the device (such as a pivoting component discussed infra), and may be selected to have hardness and compliance to provide for optimal sealing when the moisture barrier sealing system is in its sealing configuration. Elastomeric materials or co-molded surface components may be provided on any or all of the relevant sealing surfaces of the device (e.g., on all the surfaces that contact the carrier and that form part of the moisture barrier sealing system). Any or all of the seal or seals may have a molded profile to allow for the thickness of the carrier, e.g., the seal may have a slight recess for the carrier's thickness to sit in. Preferably such a recess would be slightly shallower than the thickness of the carrier.

The compliance needed in the seal material is relative, and will depend on several factors. In particular, the degree of precision in the (manufactured) parts that determine how precisely the seal and the compartment exit mate with each other, the thickness of the seal, the area of the seal that makes contact with the compartment exit, the resilience of the carrier, the use of springs and their force, and the degree of moisture protection required may all influence the selection of an optimal seal material. In certain instances the seal and compartment may mate sufficiently well so that a non-elastomeric seal material may provide satisfactory sealing and protection from moisture ingress. Suitable non-elastomeric seal materials include plastics, such as polyethylene, polypropylene, and acrylonitrile-butadiene-styrene (ABS). In one embodiment the seal and another component of the device (such as a pivoting component) may be integrally formed from a single plastic material. In another embodiment, said device component (e.g., a pivoting component) may be made of any resilient thermoplastic, such as ABS, and an elastomeric seal may be placed or molded onto said component.

The compartment may advantageously house a desiccator. The desiccator may be favorably provided in the form of a cartridge containing a water and/or moisture adsorbing material. Such water and/or moisture adsorbing materials are well known and may include activated alumina, aerogel, benzophenone, bentonite clay, calcium chloride, calcium hydride, calcium sulfate, copper (II) sulfate, lithium chloride, lithium bromide, magnesium nitrate, magnesium sulfate, magnesium perchlorate, molecular sieve(s), potassium carbonate, silica gel, sodium chlorate, sodium sulfate, sodium benzophenone. The use of such a desiccator can be easily seen in the illustrations of the exemplary embodiment in FIGS. 1 to 3, as component 108.

Favorably, the compartment is configured so that the relative humidity within the compartment is maintained at a level of about 75% or lower, more favorably 65% or lower, most favorably 60% or lower, over a period of thirty (30) days. Thirty days is a typical duration of intended patient use of a device described herein (i.e. after the patient has removed the device from any secondary packaging, such as a sealed pouch, and up to and including the last dose taken). For example, for a device containing 120 doses where two doses would be taken twice a day, the intended duration of use would be thirty 30 days. In certain instances, it has been found desirable to maintain the relative humidity within the compartment at more than a certain minimum level, in order to minimize and/or prevent unwanted electrostatic effects. Having regard to the aforesaid ranges, in such instances it is favorable to maintain a relative humidity (within the aforesaid ranges) at a level of about 20% or higher, more favorably 25% or higher, most favorably 30% or higher. For certain embodiments where the compartment may house a desiccator, in some instances it has been found desirable to pre-condition the desiccant such that the initial relative humidity in the compartment is set at a particular desired value. For example it may be desirable that the set initial relative humidity is near the low end of the desired and/or necessary relative humidity ranges, for example in the range of about 20% to about 30%, more favorably from about 25% to about 35%, still more favorably from about 30% to about 40%.

Preferably the compartment includes a single exit, i.e. the exit through which the elongate carrier will be advanced is the only opening in the compartment.

The compartment may be made by injection moulding a thermoplastic material such as high density polyethylene or a cyclic olefin copolymer. In one embodiment, the supply spool (102) with elongate tape (100) and the desiccator (108) may be loaded into the base of the compartment (105) and the tape threaded so that it is attached to the uptake spool (104). The compartment may then be closed by heat sealing a foil laminate lid (not shown) to the top of the compartment wall (106), thereby completely closing the compartment apart from at its exit (107). In an alternative configuration, the lid may be a molded plastic component that is sealed onto the top of the compartment wall, e.g., by ultrasonic welding, thermal welding, or adhesive bonding.

Desirably at least a part of, or most desirably all of, the walls of the compartment are made of a material and/or are configured such that said wall(s) provide a water vapor barrier. In particular it is desirable that said wall(s) have a water vapor transmission rate (WVTR) less than 12 g/($m^2$ day) (38° C., 90% RH), more desirably a WVTR equal to or less than 6 g/($m^2$ day) (38° C., 90% RH), even more desirably a WVTR equal to or less than 3 g/(m² day) (38° C., 90% RH), and most desirably a WVTR equal to or less than 1 g/(m² day) (38° C., 90% RH).

WVTR may be measured in accordance with a gravimetric method such as ASTM E96/E96M-05, procedure E, desiccant method at 38° C./90% relative humidity. Favorably, at least a part of, or more favorably all of, the walls of the compartment are made of a material comprising a low water vapor (moisture) permeability material, in other words a vapor barrier material. A vapor barrier material can be described as a material that, when such material has a thickness of 100 microns, has a water vapor transmission rate (WVTR) less than 12 g/(m² day) (38° C., 90% RH), in particular a WVTR equal to or less than 6 g/(m² day) (38° C., 90% RH); more particularly a WVTR equal to or less than 3 g/(m² day) (38° C., 90% RH); and most desirably a WVTR equal to or less than 1 g/(m² day) (38° C., 90% RH).

Said compartment wall(s) may be made of a single material (e.g., a vapor barrier material) or alternatively a combination of materials (e.g., different vapor barrier materials provided region-by-region or provided as a combination of layers in a wall, or alternatively vapor barrier material(s) in combination with other materials. As an example of the second mentioned alternative, the back wall and side walls may be made of a polymeric vapor barrier material (such as high density polyethylene (HDPE)), and the front wall (lid) may be made of a metal foil (such as aluminum foil or a laminated foil comprising one or more metallic layers). In another example the wall(s) of the compartment may be made of two or more layers, each layer providing different impermeability characteristics. For example, for medicament that is sensitive to long-term exposure to oxygen it may be favorable to use a material that provides desirable oxygen barrier characteristics (such as ethylene vinyl alcohol, nylon 6, nylon 66, polyvinylidene chloride, polyvinyl acetate) in conjunction with a material that provides desirable vapor barrier characteristics but typically does not provide favorable oxygen barrier characteristics (such as high density polyethylene (HDPE)). Alternatively, wall(s) of the compartment may comprise two or more layers e.g., for ease of manufacturing, and/or for stability. For example, wall(s) of the compartment may be made of an aluminum foil laminated to a suitable polymer layer or alternatively sandwiched between two appropriate polymer layers or alternatively aluminum may be deposited onto an appropriate polymer layer (e.g., creating a metalized polyethylene terephthalate layer or metalized nylon layer) or alternatively two metalized plastic layers (e.g., aluminum deposited on polyethylene or polypropylene) may be laminated together with the metalized surfaces facing each other. Another alternative is the lamination of a polymeric vapor barrier layer onto another polymeric layer inter alia for strength. In addition, wall(s) of the compartment may comprise an outer layer made of a vapor barrier material and an inner layer comprising a desiccant material. This could be done, for example, using a two-shot molding process where the outer layer is a polymer with low vapor transmission rate (e.g., HDPE, polypropylene (PP), or a cyclic olefin copolymer) and the inner layer is a desiccating polymer (e.g., Nylon), or alternatively the outer layer could be made of a polymeric vapor barrier material, whose interior surface is lined with a nonwoven embedded with desiccant particles. In regard to the latter the material of the desiccant particles can be selected from the aforesaid list of materials. Additional examples of combinations include a blending of a vapor barrier material (e.g., PE) with another material (e.g., ethylene-vinyl acetate (EVA))

Suitable vapor barrier materials may include metal foil, in particular aluminum foil have a thickness of at least 8 microns, more particularly at least 10 microns, even more particularly at least 15 microns, most particularly at least 25 microns. The desired and/or necessary thickness depends on how the foil is used. For example aluminum foil laminated between layers of polymeric vapor barrier layers may only need to be 8 microns thick, while for plain aluminum foil it may be desirable and/or necessary to use a foil having a thickness of 25 microns or more. The lid may desirably be 80 microns thick, including an aluminum foil layer of 8 microns sandwiched between layers of low density polyethylene and with an outer coating of polyethylene terephthalate. Other suitable vapor barrier materials may include coatings, such as deposited aluminum coatings (in particular having a thickness of at least 0.1 microns), deposited silicon oxide coatings (in particular having a thickness of at least 0.04 microns), deposited diamond-like glass coatings (such coatings, and methods to produce such coatings, are described in U.S. Pat. No. 6,696,157 (David et al.) the content of which is incorporated here in its entirety). Further suitable vapor barrier materials may include polymeric materials such as polyvinylchloride (hard or plasticized, in particular hard PVC); ethylene vinyl alcohol (in particular ethylene vinyl alcohol having a high ethylene content, more particularly an ethylene content of at least 30%); polyacrylonitrile; polyethylene terephthalate; polyethylene naphthalate; polyolefins (in particular polypropylene, copolymers of polypropylene with polyethylene, biaxially orientated polypropylene; polyethylene (including low density polyethylene (density equal to or less than 0.925 g/cm³)), linear low density polyethylene, medium density polyethylene (density greater than 0.925 g/cm³ and less than or equal to 0.94 g/cm³), high density polyethylene (density greater than 0.94 g/cm³); cyclic olefin copolymers (e.g., such as those commercially available under the trade designation TOPAS); poly-vinylidene chloride; polychlortrifluorethylene; and liquid crystal polymers. Among polyethylenes, high density polyethylenes are particularly advantageous as a vapor barrier material. Polymers, in particular polyolefins (including low density polyethylene, linear low density polyethylene, medium density polyethylene, high density polyethylene, polypropylene, biaxially orientated polypropylene) produced using metallocene catalysts are favorable in that the use of such catalysts generally allows for the production of polymers having narrower molecular weight distributions than does the use of more traditional Zeigler-Natta catalysts, and thus allows for a better, tighter control over composition and in turn vapor barrier characteristics.

As applicable, walls of the compartment or parts of walls may be produced via injection molding (e.g., single shot or multi-shot molding) as well as other methods including co-extrusion, extrusion lamination, vacuum metallization, or a combination of methods as desired and/or needed.

It may be desirable, depending on the choice of wall material(s) and the particular medicament(s), to provide at least a part of or, more desirably all of, the walls of the compartment with a greater thickness than commonly used in such devices, without adding so much material as to make the device unwieldy. In particular, for wall materials that are not foil-based (e.g., not metal-foil-based, nor polymer and metal-foil laminate based), it may be desirable to provide at least a part of, or more desirably all of, the walls of the compartment with a thickness of greater than or equal to about 500 microns, more desirably greater than or equal to about 1000 microns, most desirably greater than or equal to about 1250 microns. It is also desirable to provide at least a part of, or more desirably all of, the walls of the compartment with a thickness of less than or equal to 4 mm, more desirably less than or equal to 3 mm, most desirably less than or equal to 2 mm.

As mentioned above the compartment may be favorably provided within a cassette that is reversibly removable from the dry powder inhaler. Such a cassette would favorably include also an uptake spool, so that the user can easily insert the cassette into the dry powder inhaler and/or easily remove the cassette. For long storage as an original and/or a re-fill supply unit, the cassette may be sealed in a container, such as a pouch.

Figure 7:
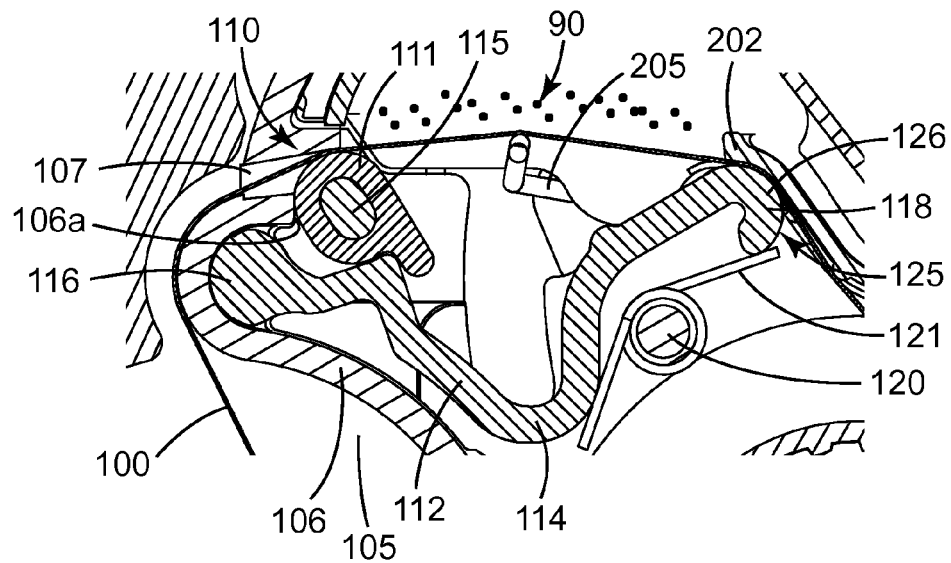

FIG. 7 is an illustration of the region about the compartment exit and the lower portion of the chamber of the exemplary inhaler at the point of actuation, i.e. where powder associated with the dose-release area is released from the carrier for inhalation by the patient through the patient port.

Various means for releasing powder from an area of carrier independent of the patients' inspiratory effort are known. A number of such means are disclosed in U.S. Pat. No. 5,619,984 (Hodson et al.), including systems providing mechanical effort, e.g., impaction, vibrations, gas flow etc., or electrostatically. The means for releasing powder from the carrier during inhalation is favorably triggered in response to the patient inhaling, in order to avoid the patient having to synchronise actuation of the release mechanism with inhalation. Airflow detection may conveniently be accomplished by means of a movable vane positioned within the chamber or patient port, motion of the vane causing actuation of the release mechanism.

In the exemplary embodiment, the release of powder is triggered in response to the patient inhaling. In particular, upon inspiration by the user a movable vane (not visible; an outer portion of a vane positioning pin (201) can be seen in FIGS. 1 to 3) within the chamber releases a trigger mechanism (not visible) that in turn releases a hammer (205; visible in FIGS. 4 to 7). The hammer then strikes the carrier (100), so that the powder (90) associated with the dose-release area is released into the chamber (200) (as illustrated in FIG. 7).

It has been found particularly advantageous to have the dose-release area of the carrier (i.e. that area of the portion of the carrier that has been advanced to within the chamber for powder release) be clamped between a first and a second clamping system. As mentioned above, by clamping the area of the carrier to be impacted between two clamping systems, during actuation, it is possible to reduce and/or prevent powder from other areas of the carrier (i.e. those areas either behind or ahead of the intended dose-release area) from being dislodged when the powder associated with the dose-release area is released. This advantageously allows for improved reproducibility of the emitted dose.

The double clamping can be achieved by providing a first clamping system and a second clamping system, wherein the first and second clamping systems are configured and arranged such that they are moved into a clamping configuration at least prior to release of the powder associated with the dose-release area, so that said area of the carrier will be clamped between the first and the second clamping systems during release of the powder associated with said area of the carrier. As mentioned supra, an aspect of the present invention includes dry powder inhalers which include such a double clamping system, but do not make use of a moisture-barrier sealing system. Also as mentioned supra, certain embodiments in accordance with certain other aspects of the present invention include inhalers and/or cassettes including such a double clamping system in addition to a moisture barrier sealing system.

For certain embodiments of inhalers and/or cassettes in accordance with the present invention that include a moisture barrier sealing system that is configured and arranged such that the sealing system is returned to its sealing configuration at least prior to release of the powder associated with the dose-release area, the double clamping can be achieved in an alternative way, i.e. where the moisture barrier sealing system acts as a clamping system. Such embodiments would include a clamping system in addition to the moisture barrier sealing system, said clamping system being configured and arranged such that it is moved into a clamping configuration at least prior to release of the powder associated with the dose-release area and wherein said clamping system and said moisture barrier sealing system are configured and arranged relative to one another such that said dose-release area will be clamped between the clamping system and the moisture barrier sealing system during release of the powder associated with the dose-release area. In other words the dose-release area is positioned between the moisture barrier sealing system and a second clamping system and is clamped by the two systems prior to dose release.

This latter alternative may be better appreciated by looking at the exemplary embodiment. As described in conjunction with FIGS. 4 to 6, the moisture barrier sealing system (110), in particular its seal (111), in its sealing configuration seals the exit (107) of the compartment (105) and at the same time clamps the carrier (100) against the wall (106) of the compartment (105), between the seal (111) and the outer surface (106a) of the compartment wall (106). See e.g., FIGS. 6 and 7 in comparison to FIG. 5. So in the exemplary embodiment the moisture barrier sealing system also acts as a clamping system. The exemplary embodiment includes an additional clamping system (125), where in its clamping configuration (see again FIGS. 6, and 7 in comparison to FIG. 5), the carrier (100) is clamped via a grip (126) of the clamping system (125) against the outer surface (202a) of the chamber wall (202). Referring to FIG. 7, it will be appreciated that the area of carrier (100) that was advanced to within the chamber (200) is clamped between the two systems. In this embodiment the leading end of said area is clamped by the grip (126) of the clamping system and the trailing end by the seal (111) of the moisture barrier sealing system. When the hammer (205) strikes the carrier (100) to release the powder (90) associated with the area of the carrier that is positioned between the clamps, transfer of energy from that area of the carrier to other areas of the carrier (areas ahead or behind the area of the carrier within the chamber that is intended for dose release when impaction by the hammer occurs) is minimized and/or prevented. In this manner, unwanted release of powder from areas of the carrier still within the supply compartment (105) may be minimized and/or prevented, as may unwanted release of any residual and/or remaining powder from areas of used carrier already in the uptake area.

In the exemplary embodiment, the second clamping system (125) is formed as an extension (118) of a pivoting component (112) that is used in the moisture barrier sealing system (110).

Here reference is made to FIGS. 8 to 11 showing a partial cross-sectional, detailed view (now without the cover) of the region including the supply and uptake spools, compartment exit and flow chamber of the exemplary inhaler at closed (FIG. 8), partially open (FIG. 9), between partially & fully open (FIG. 10) and fully open (FIG. 11) positions, respectively. (FIGS. 8, 9 and 11 correspond to FIGS. 1, 2, and 3, respectively, as well as to FIGS. 4, 5 and 6, respectively.)

The pivoting component (112) has a front-plate (113) with a quasi triangular structure (see e.g., FIGS. 8 to 11) and a quasi-V-shaped rib back-structure (114) plus a pin-like structure (115) onto which the seal (111) is affixed (see FIGS. 4 to 7). One end of the aforementioned quasi-V-shaped rib back-structure (the one distal to the seal (111)) provides the grip (126) of the clamping system. The other end is provided in the form of a partial cylinder (116). The pivoting component (112) is held in place by a pin (not visible) that protrudes from the back of the partial cylinder (116), the pin being retained within a suitable cylindrical hole in the main frame or chassis of the inhalation device. The partial cylinder (116) is positioned within a "socket" in the curve of the compartment wall (106). There is clearance between the partial cylinder (116) and the "socket", and as can be seen in the Figures the partial cylinder "rotates/pivots" in the "socket". Moreover, comparing FIGS. 8 to 11 it can be seen that the pivoting component (112) pivots about an axis (P) generally perpendicular to the front-plate (113), the axis (P) falling within the partial cylinder (116) near but spaced apart from the seal (111). (Relative to the printed illustration the axis (P) is perpendicular to the page of the illustration and is to the left and below the seal.)

Figure 8:
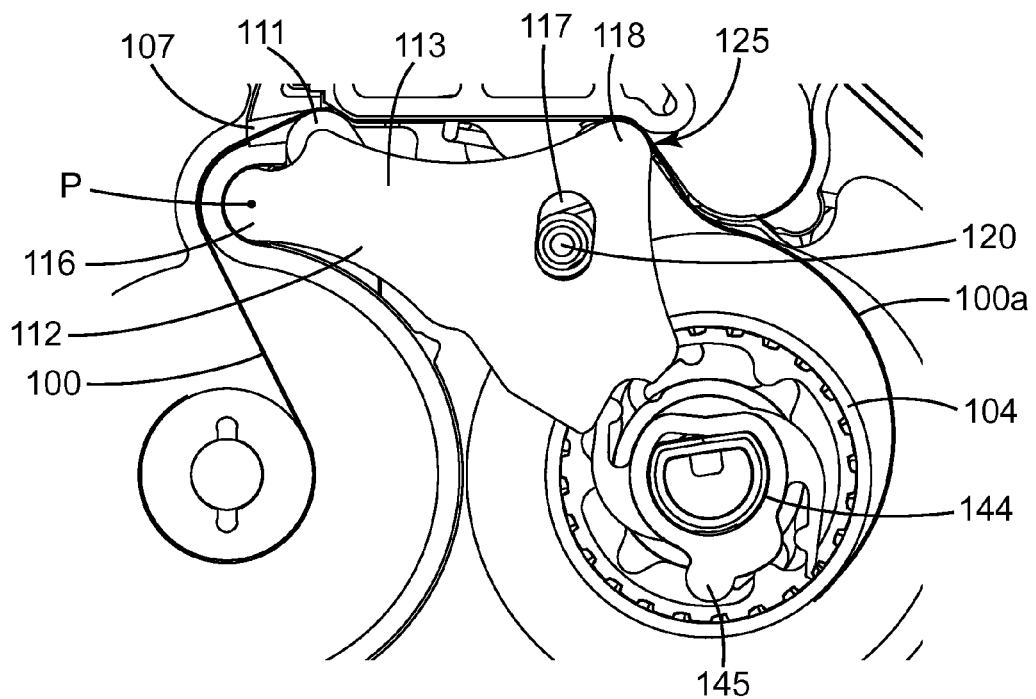
FIGS. 8 to 11 represent partial cross-sectional illustrations of an additional particular region of the exemplary dry power inhaler in its closed position, a partially open position, a yet further, but not fully opened position and its fully opened position, respectively.

As can be best seen in FIGS. 4 to 7 the exemplary embodiment includes a post (120) and a torsional spring (121). The post (120) is positioned near the quasi-V-shaped rib back-structure but on the far side relative to the seal (111). The torsional spring (121) engages portions of the back-structure (114) of the pivoting component (112) and provides force onto said pivoting component such that the seal (111) is biased towards its sealing configuration, sealing off the exit (107) of the compartment (105). Comparing for example FIGS. 4 and 5, it can be recognized that the torsional spring (121) is providing a substantially counterclockwise force on to the pivoting component. The pivoting action of the pivoting component is limited by providing a slot (117) in the front-plate structure and having one end of the post (120) extending through the slot. With reference to FIG. 8—the closed position of the exemplary inhaler—the post (120) is located adjacent to the bottom of the slot (117), the seal (111) is sealing off the exit (107) and at the same time clamping the carrier (100) against the outer surface of the compartment, and the portion of the carrier near and around (100a) the uptake spool (104) is slack.

Figure 9:
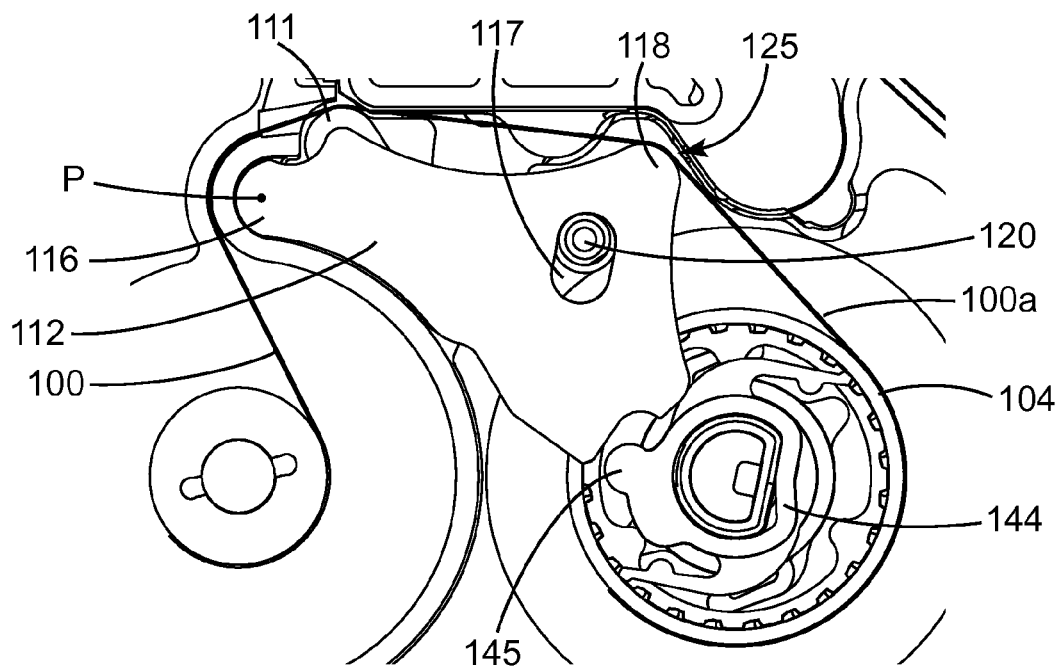

As the user opens the mouthpiece cover (301 in FIGS. 1 to 3) of the exemplary inhaler, as can be seen in FIG. 9—the partially open position of the mouthpiece cover—the uptake spool turns in a clockwise direction and the outer turn of carrier about the uptake spool is drawn tight. The newly created tension of the carrier (100), and thus force, against the end of the upper extension/grip (118; visible in FIG. 9/126; not visible in FIG. 9) of the pivoting component (112) (in particular against the end of the upper portion of the back structure, referred to above as the grip (126)) overcomes the force from the torsional spring (121), thus causing the pivoting component (112) to rotate in a substantially clockwise direction, and at the same time causing the moisture barrier sealing system to relax (move out of its sealing configuration) thereby causing the exit (107) of the compartment (105) to be unsealed. With reference to FIG. 9, the post (120) is adjacent to the top of the slot (117), the seal (111) has shifted slightly clockwise and downward, the carrier is advancing over the seal (111) and over the grip (126, not visible) and the uptake spool has rotated clockwise by about 90-100 degrees from its illustrated position in FIG. 8 to its illustrated position in FIG. 9. The latter is best seen and understood through reference to the movement of a quasi-semi-circular cam feature (145) on the forward ratchet (144) on the uptake spool (104), which indicates that said uptake spool has rotated clockwise by about 90-100 degrees.

Figure 10:
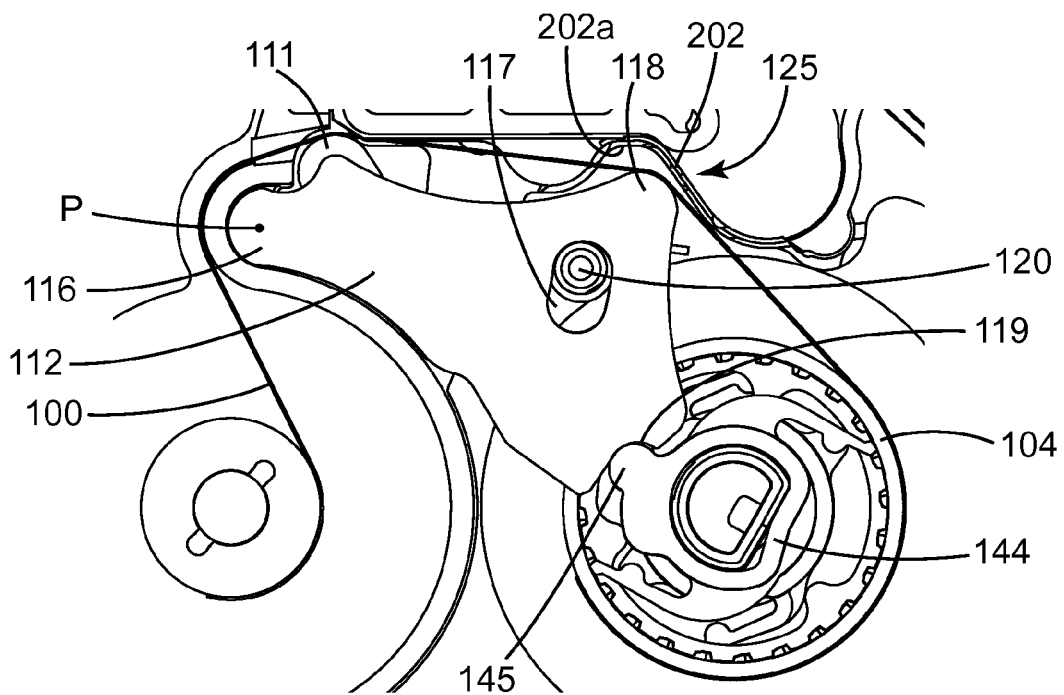
Figure 11:
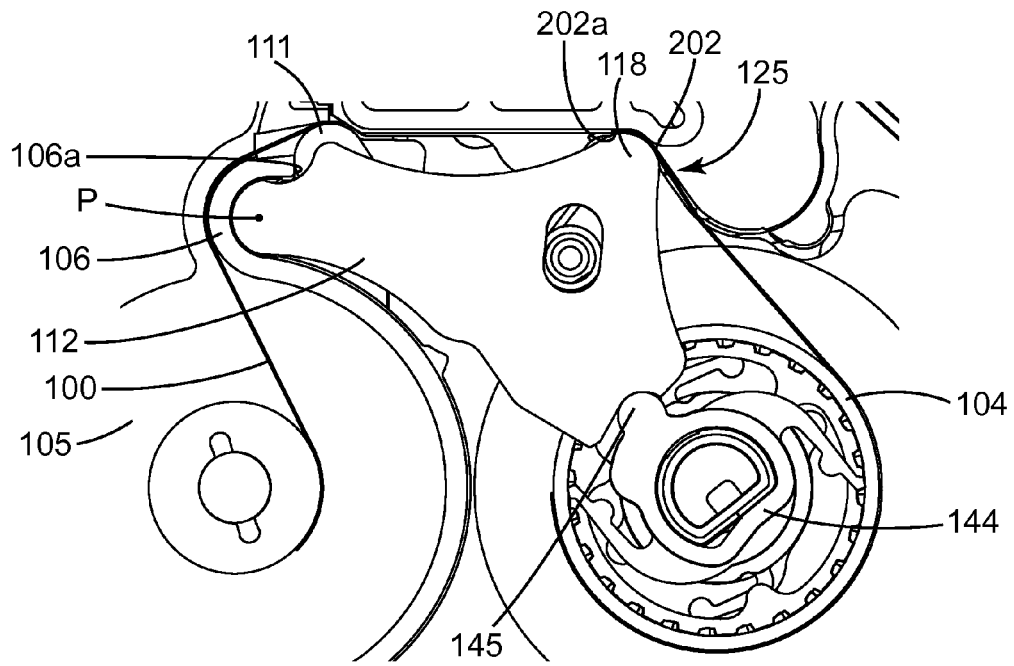

As the user continues to open the mouthpiece cover (301) of the exemplary inhaler to a position between partially open and fully open—as can be seen in FIG. 10—the uptake spool continues to turn in a clockwise direction and the aforementioned cam (145) on the forward ratchet (144) begins to engage a heel (119) of the pivoting component (112), thereby urging the pivoting component to rotate/pivot counter-clockwise and moving the grip (126) of the clamping system (125) towards the chamber wall (202). Finally as the user opens the mouthpiece cover (301) completely (to the fully open position as illustrated in FIG. 11), the grip (126) of the clamping system (125) is at last fully engaged with the carrier (100)/chamber wall (202) (i.e. clamping the carrier (100) against the outer surface (202a) of the chamber wall (202)) and the seal (111) of the moisture barrier system is engaged with the carrier (100)/compartment wall (106) (i.e. clamping the carrier (100) against the outer surface (106a) of the compartment wall (106)), so that the dose-release area is clamped between the seal (111) and the grip (126). The presence of an elastomeric seal (111) in the moisture barrier sealing system (110) enables this seal (111) to seal against the surface (106a) of the compartment wall (106) before the grip (126) of the clamping system (125) fully seals against the surface (202a) of the chamber wall (202). The use of cam (145) and its engagement against the heel (119) of the pivoting component (112) facilitates the sealing of the grip (126) against the chamber wall (202). The exemplary inhaler is now ready for release of the powder associated with the dose-release area (said release already having been described in conjunction with FIG. 7).

In alternative embodiments, the pivoting component (112) may be substituted by a component that moves linearly to clamp and unclamp the carrier, said component being located and arranged in any suitable manner that will be apparent to one skilled in the art who has studied the present disclosure and exemplary embodiment.

A clamping system may comprise a grip or grips. Desirably such grip(s) have a form and comprise a material suitable for appropriately clamping the carrier. Suitable materials for a clamping system grip may have a Shore A hardness equal to or less than 85, in particular equal to or less than 75 (as determined by ASTM test number D2249). Suitable materials for a clamping system grip may have a Shore A hardness equal to or greater than 35, in particular equal to or greater than 45 (as determined by ASTM test number D2249). A grip may be made of the same material as another (e.g., pivoting) component, so that it is contiguous with that component. Alternatively, a grip may comprise an elastomeric material, e.g., an elastomeric grip component affixed to the pivoting component in much the same way as the moisture barrier seal is affixed to the pivoting component. As other options, the grip may be 2-shot molded to the pivoting component. Since it is believed that one of the functions of the double clamping is to prevent or reduce vibrations of the carrier, by absorbing some or all of their energy, which occur during release of powder from the dose-release area, from being transferred to regions of the carrier outside the dose-release area, this may be facilitated by using an elastomeric material (in particular such a material having a lower Shore A hardness value e.g., around 35 to 55) for both the grip(s) and the seal of moisture barrier sealing system, as applicable. Increasing the distance along the area of the carrier that the clamps operate could be more effective in damping. However such parameters would need to be optimized with other performance considerations for the device, e.g., disturbance of powder by contact with the clamps and/or the need to advance lengths of carrier much longer than the length of the dose-release area.

In particularly favorable embodiments of devices in accordance with certain aspects described herein the moisture barrier sealing system is configured and arranged such that the sealing system is returned to its sealing configuration upon cessation of advancement of the carrier. The general functioning of such particularly favorable embodiments may be as follows: whenever the patient is advancing the carrier by exerting force on a user-operated advancing element (such as by pulling/holding the mouthpiece-cover open in the exemplary inhaler; alternative user-operated advancing elements may include buttons or levers), the carrier is placed under tension (part of said patient-exerted force is transmitted via appropriate device components into tension in the carrier), said tension causing the moisture barrier sealing system to disengage, opening the compartment exit thereby allowing carrier to pass easily through the exit. Upon cessation of advancement of the carrier (in other words as soon as the patient ceases to exert force on the user-operated advancing element), the tension in the carrier is relieved or reduced and the carrier goes slack, causing the moisture barrier sealing system to return to its sealing position (e.g., under its own accord (e.g., due to elastic resilience) or under the influence of a separate component (such as a torsional spring (as in the exemplary inhaler)). Such embodiments are particular advantageous in that the medicament supply compartment is only un-sealed wherever it is needed to advance the carrier, and sealed whenever it does not need to be unsealed to allow tape advance, said sealing and unsealing being "automatic" and not compromised by forgetfulness nor confusion on the part of the patient. Additional benefits of such a sealing arrangement are that whenever tape is not being advanced the medicament supply compartment is protected against moisture ingress from the exhaled breath if that is inadvertently exhaled into the inhaler device, and also that any drug powder that may come loose from the supply of tape cannot escape from the medicament supply compartment.

In the exemplary inhaler described herein, the moisture barrier sealing system, in particular the seal thereof, is favorably coupled to a pivoting member that is engaging a spring, said spring urging the pivoting member in a direction such that the moisture barrier seal seals the compartment exit, and wherein upon advancement of the carrier under the tension associated with the advancement of the carrier the pivoting member rotates in the opposite direction, so that the moisture barrier seal disengages, opening the compartment exit thereby allowing carrier to advance through the exit, and upon cessation of advancement of the carrier, under the tension of the spring the pivoting member rotates in its original direction, so that the moisture barrier seal seals the compartment exit.

Figure 12:
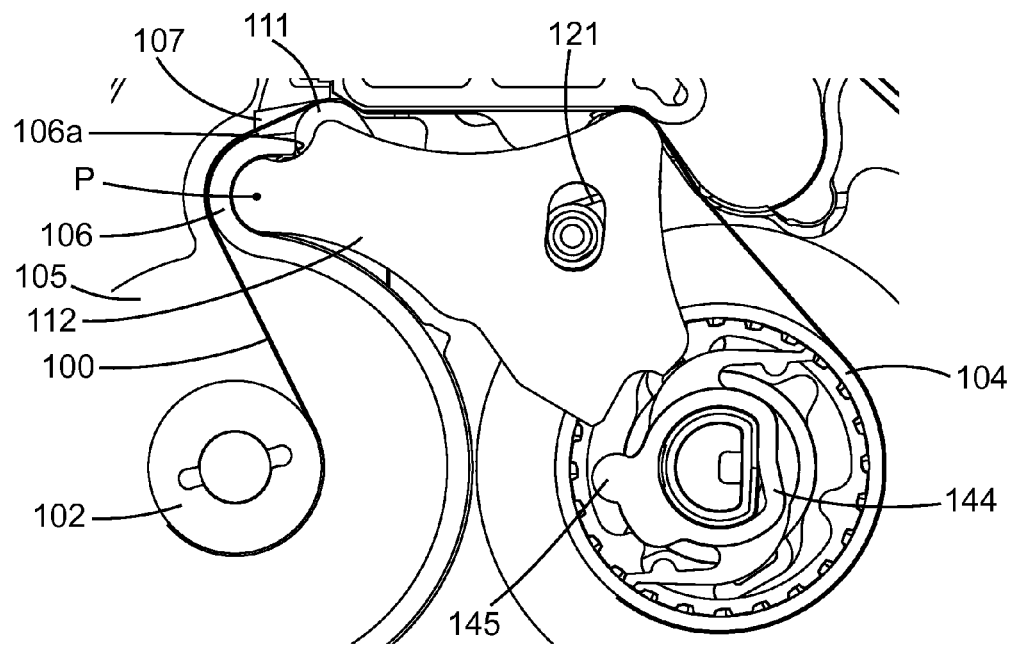
FIG. 12 represents a partial cross-sectional illustration of an additional particular region of the exemplary dry power inhaler in its sealed position after stopping opening mid-way.

FIG. 12 shows a sealed position of the exemplary inhaler reached by a user who has stopped advancing the carrier (i.e. who has stopped pulling/holding the mouthpiece-cover (301) open) after having advanced it partially. Upon letting go of the mouthpiece-cover, the tension in the carrier (100) has caused the mouthpiece-cover (301), forward ratchet and uptake spool (104) to rotate counter-clockwise by about 10 degrees or so. This back rotation relieves tension in the carrier (100) and creates enough slack in it for the pivoting component (112) to rotate counter-clockwise under the force of the torsional spring (121) until the seal (111) of the moisture barrier sealing system re-engages with the compartment wall (106) and thus re-seals the exit slot (107) of the compartment (105).

As mentioned above, the elongate carrier may be wound on a spool within the supply compartment. It is desirable that the spool comprises an anti-unspooling mechanism. An anti-unspooling mechanism, which could utilize a friction brake, a ratchet system, or some other mechanism to prevent unspooling of the carrier, desirably reduces or prevents any rotation of the supply spool not associated with advancement of the carrier. An anti-unspooling mechanism also favorably provides resistance to movement of the elongate carrier while it is being advanced, in particular just after the moisture barrier sealing system has relaxed. This resistance to movement facilitates the creation/maintenance of tension in the carrier during advancement of the carrier.

Figure 13:
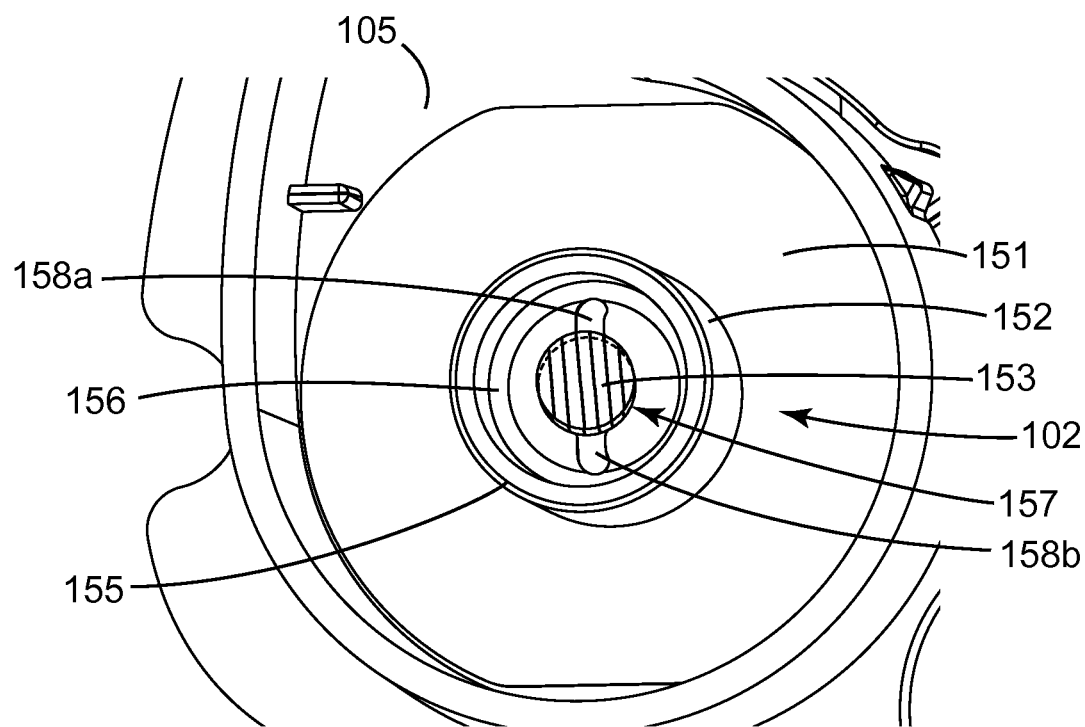
FIG. 13 represents an isometric view of part of the compartment of the exemplary dry powder inhaler, showing the supply spool and the friction brake.
Figure 14:
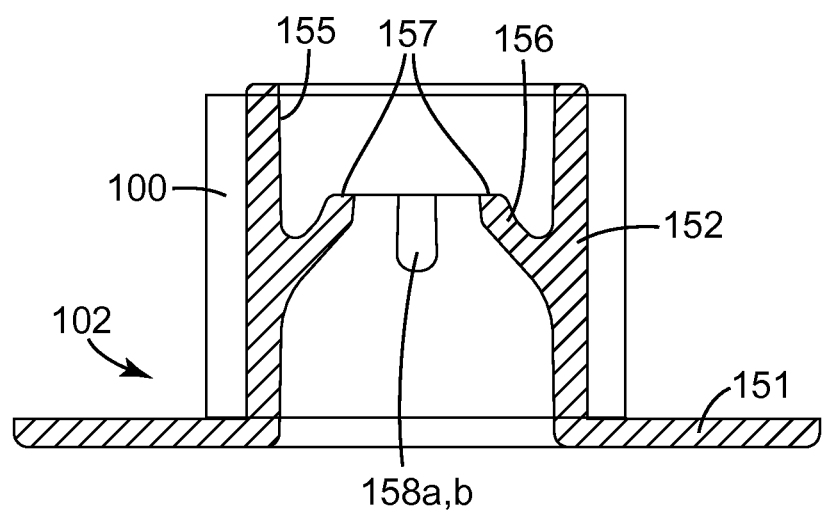
FIG. 14 represents a partial cross sectional illustration of the region of the supply spool with the elongate carrier wound on it, plus the outer component of the friction brake.

Such a mechanism may be best understood by reference to FIGS. 13 and 14, providing an isometric view of part of the compartment of the exemplary dry powder inhaler, showing the supply spool and the anti-unspooling mechanism, in particular a friction brake, and a partial cross sectional illustration of the region of the supply spool with elongate carrier wound on it, plus the outer component of the friction brake, respectively. The supply spool (102) has the elongate carrier (100), preloaded with finely divided powder wound thereon. As can be seen from FIGS. 13 and 14, the lower part of the supply spool has an annular flange (151) to retain the carrier and a cylindrical core (152) around which the elongate carrier is wound. The compartment (105) has a supply post (153) which provides an axle for the supply spool (102) to rotate about. The supply post is generally cylindrical, with a smooth surface. As an alternative, the surface of the supply post may be splined, with splines arranged uniformly about the circumference directed parallel to the axis. The interior (155) of the cylindrical core has an inwardly upwardly directed lip (156) extending from about half way up and arranged to contact the supply post to provide an interference with frictional properties at the contact region (157). The lip has two diametrically opposite wide slits (158a,b) extending from the contact region (157) part of the way back to the cylindrical core (152). These slits allow the lip to pull away from the supply post slightly under the influence of the interference fit, but be retained by the elastic properties of the supply spool material. Where the supply post is splined, the contact region of the lip may also have splines. The two sets of splines allow the supply spool to rotate on the supply post only when the post splines push the spool splines back a small amount, causing the spool to click round in defined small increments during use. The friction brake is provided by the interference in the contact region (157) and ensures that the elongate carrier remains tightly wound on the supply spool during use.

Finely divided powders used in the devices described herein generally have a mass median particle diameter typically 10 microns or less. More suitably, said mass median diameter is 7 microns or less, even more suitably 5 microns or less, and most suitably said mass median diameter is in the range 1 to 3 microns, with at least 90% by mass of the particles having diameters below 5 microns.

The powders may be micronized, e.g., by using a fluid energy mill driven by compressed air, such as shown in 'Drug Delivery to the Respiratory Tract' ed. D. Ganderton and T. Jones, publ. Ellis Horwood, Chichester (1987) pages 89-90, or by repeated stepwise millings or by use of a closed loop milling system.

As indicated supra, desirably finely divided powder is filled into a plurality of microdepressions in the surface of an elongate carrier, in particular a flexible elongate carrier, such as a web or a tape. Depressions may be suitably spaced at an interval of about 20 to 2000 microns, more suitably at an interval of about 300 to 2000 microns. Depressions may suitably number from about 25 to 1000 per $cm^2$ of the carrier. The volume of each depression and the spacing or number of the depressions will depend upon the particular desired application of the resulting filled elongate carrier, and in the case of biologically active substances (e.g., medicaments) the potency of the particular substance and the area of the carrier material intended to provide a single dose of the substance. Typically it is desirable that the carrier material has a substantially uniform depression volume per unit area when considered on a scale of the area of a single dose or other functional unit. For example, such a dose area might have 200 to 2000 discrete microdepressions, each of about 45 microns depth and about 150 microns diameter. Advantageously, the rows of microdepressions along the longitudinal axis of the elongate carrier do not lie exactly parallel with the axis, but instead lie skewed at a small angle (e.g., 0.5° to 2°) to it, in order to avoid "quantization effects" caused by lateral variability in the slitting positions. (The skew angle can be chosen appropriate to the microdepression spacing distance and the desired slit width, such that an exact total microdepression volume is present on each (e.g., 20 mm×10 mm) dose area, no matter where slitting occurs, laterally.) Preferably, the microdepressions are provided by cast embossing of a low density polyethylene (LDPE) layer using a photolitho-graphically patterned and etched, or a diamond machined, patterning roller. Suitably the aforesaid LDPE layer is provided on a paper backing or a paper/LDPE laminate backing (with the paper between the two LDPE layers).

Such filled elongate carriers are particularly conveniently be used in the administration of biologically active substances, in particular medicaments by inhalation. Moreover, elongate carriers having microdepressions can be substantially accurately and uniformly filled with such finely divided powders e.g., through methods disclosed in WO 2007/112267 (Hodson and Wilby) (the content of which is incorporated in its entirety by reference), thus allowing for accurate and uniform release of doses of biologically active substances.

For delivery by inhalation, suitable medicaments include any drug or drug combination that may be administered by inhalation, that is a solid or that may be incorporated in a solid carrier. Suitable drugs include those for the treatment of respiratory disorders, e.g., bronchodilators, anti-inflammatories (e.g., corticosteroids) anti-allergics, anti-asthmatics, anti-histamines, and anti-cholinergic agents. Other drugs such as anorectics, anti-depressants, anti-hypertensive agents, antineoplastic agents, anti-tussives, anti-anginals, anti-infectives (e.g., antibacterials, antibiotics, anti-virals), anti-migraine drugs, anti-peptics, dopaminergic agents, analgesics, beta-adrenergic blocking agents, cardiovascular drugs, hypoglaecemics, immunomodulators, lung surfactants, prostaglandins, sympathomimetics, tranquilizers, steroids, vitamins and sex hormones, vaccines and other therapeutic proteins and peptides may be employed for delivery by inhalation.

It is preferred for delivery by inhalation that the medicament employed exhibits a potency which permits a single dose to be loaded onto the elongate carrier in an area of less than about 25 cm$^2$ and preferably less than about 5 cm$^2$. More preferred is an elongate carrier containing a drug in such a manner and of such a type that between 0.25 and 2.5 cm$^2$, most preferably between 1.5 and 2.25 cm$^2$, of the elongate carrier will contain a single dose when used in a device such as those described in U.S. Pat. No. 5,408,994 or 5,619,984. Stated differently, given that a filled elongate carrier may conveniently carry between about 25 and 500 μg of powder per cm$^2$, the potency of the medicament will preferably be such that a single dose may be carried on the above-stated 0.25 to 2.5 cm$^2$ of elongate carrier.

Exemplary drugs which may be employed for delivery by inhalation include but are not limited to: albuterol, levalbuterol, terbutaline, fenoterol, metaproterenol, isoproterenol, isoetharine, bitolterol, epinephrine, tulobuterol, bambuterol, reproterol, adrenaline, ipratropium, oxitropium, tiotropium, daratropium, aclidinium, glycopyrronium, beclomethasone, butixocort, betamethasone, flunisolide, budesonide, mometasone, ciclesonide, rofleponide, aminophylline, dyphylline, theophylline, cromolyn sodium, nedocromil sodium, ketotifen, azelastine, ergotamine, cyclosporine, salmeterol, fluticasone, formoterol, arformoterol, procaterol, indacaterol, TA2005 (carmoterol), omalizumab, montelukast, zafirlukast, betamethasone sodium phosphate, dexamethasone, dexamethasone sodium phosphate, dexamethasone acetate, prednisone, methylprednisolone acetate, oglemilast, zileuton, insulin, atropine, prednisolone, benzphetamine, chlorphentermine, amitriptyline, imipramine, clonidine, actinomycin c, bromocriptine, fentanyl, buprenorphine, pentamidine, calcitonin, leuprolide, alpha-1-antitrypsin, interferons, human growth hormones, propranolol, lacicortone, triamcinolone, dinoprost, xylometazoline, diazepam, lorazepam, folic acid, nicotinamide, clenbuterol, ethinyloestradiol, levonorgestrel, and pharmaceutically acceptable salts and esters thereof such as albuterol sulfate, formoterol fumarate, salmeterol xinafoate, aclidinium bromide, glycopyrronium bromide, beclomethasone dipropionate, triamcinolone acetonide, fluticasone propionate, fluticasone furoate, tiotropium bromide, leuprolide acetate and mometasone furoate.

Further drugs that may also be delivered by inhalation include but are not limited to aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, fentanyl citrate, oxycodone hydrochloride, codeine phosphate, dihydrocodeine bitartrate, pentazocine hydrochloride, hydrocodone bitartrate, levorphanol tartrate, diflunisal, naltrexone, oxycodone, sufentanil, remifentanil, diamorphine, trolamine salicylate, methadone hydrochloride, nalbuphine hydrochloride, nalorphine, tetrahydrocannabinol, mefenamic acid, butorphanol tartrate, choline salicylate, butalbital, phenyltoloxamine citrate, diphenhydramine citrate, methotrimeprazine, cinnamedrine hydrochloride, meprobamate, ergotamine tartrate, propanolol hydrochloride, isomethepene mucate, dichloralphenazone, sumatriptan, rizatriptan, zolmitriptan, naratriptan, eletriptan, barbiturates (e.g., pentobarbital, pentobarbital sodium, secobarbital sodium), benzodiazepines (e.g., flurazepam hydrochloride, triazolam, tomazeparm, midazolam hydrochloride, lorazepam, buspirone hydrochloride, prazepam, chlordiazepoxide hydrochloride, oxazepam, clorazepate dipotassium, diazepam, temazepam), lidocaine, prilocalne, xylocalne, beta-adrenergic blockers, calcium channel blockers (e.g., nifedipine, diltiazem hydrochloride, and the like), diuretics (e.g., amiloride, furosemide), nitrates (e.g., nitroglycerin, isosorbide dinitrate, pentaerythritol tetranitrate, erythrityl tetranitrate), hydroxyzine pamoate, hydroxyzine hydrochloride, alprazolam, droperidol, halazepam, chlormezanone, haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, lithium carbonate, bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, colchicine, allopurinol, heparin, heparin sodium, warfarin sodium, urokinase, streptokinase, altoplase, aminocaproic acid, pentoxifylline, empirin, ascriptin, valproic acid, divalproate sodium, phenytoin, phenytoin sodium, clonazepam, primidone, phenobarbitol, phenobarbital sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, ethosuximide, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, hydroxyzine hydrochloride, diphenhydramine hydrochloride, chlorpheniramine maleate, brompheniramine maleate, clemastine, azelastine, cyproheptadine hydrochloride, terfenadine citrate, loratidine, clemastine, triprolidine hydrochloride, carbinoxamine maleate, diphenylpyraline hydrochloride, phenindamine tartrate, lamivudine, abacavir, acyclovir, gancyclovir, valganciclovir, cidofovir, foscarnet, azatadine maleate, tripelennamine hydrochloride, dexchlorpheniramine maleate, methdilazine hydrochloride, trimprazine tartrate, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, calcitonin, parathyroid hormone, acitretin, amikacin sulfate, aztreonam, benzydamine, calcipotriol, chloramphenicol, chloramphenicol palmitate, chloramphenicol sodium succinate, ciprofloxacin hydrochloride, clindamycin hydrochloride, clindamycin palmitate, clindamycin phosphate, efalizumab, reslizumab, mepolizumab, anrukinzumab, metronidazole, metronidazole hydrochloride, gentamicin sulfate, lincomycin hydrochloride, tobramycin sulfate, tacrolimus, vancomycin hydrochloride, polymyxin B sulfate, colistimethate sodium, colistin sulfate, tetracycline, griseofulvin, keloconazole, interferon gamma, zidovudine, amantadine hydrochloride, ribavirin, acyclovir, pentamidine e.g., pentamidine isoethionate, cephalosporins (e.g., cefazolin sodium, cephradine, cefaclor, cephapirin sodium, ceftizoxime sodium, cefoperazone sodium, cefotetan disodium, cefutoxime axotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, GM-CSF, ephedrine, pseudoephedrine, ammonium chloride, androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), levothyroxine sodium, human insulin, purified beef insulin, purified pork insulin, glyburide, chlorpropamide, glipizide, tolbutamide, tolazamide, rosiglitazone, pioglitazone, troglitazone, clofibrate, dextrothyroxine sodium, probucol, lovastatin, rosuvastatin, niacin, DNase, alginase, superoxide dismutase, lipase, calcitonion, alpha-1-antitrypsin, interferons, sense or anti-sense nucleic acids encoding any protein suitable for delivery by inhalation, erythropoietin, famotidine, cimetidine, ranitidine hydrochloride, omeprazole, esomeprazole, lanzoprazole, meclizine hydrochloride, nabilone, prochlorperazine, dimenhydrinate, promethazine hydrochloride, thiethylperazine, scopolamine, sildenafil, vardenafil, cilomilast, imiquimod or resiquimod. Where appropriate, these drugs may be delivered in alternative salts forms.

The medicament may comprise one or more drugs, having one or more particulate forms, and may include one or more physiologically acceptable or inert excipients.

The invention claimed is:

1. A dry powder inhalation device comprising:
   a chamber; a patient port in communication with said chamber;
   a compartment housing an elongate carrier preloaded with a plurality of doses of finely divided powder comprising a biologically active substance, said powder being releasably retained on a surface of the carrier, said compartment being configured such that said preloaded doses are sealed within said compartment and such that the carrier may be advanced from the compartment to the chamber through an exit provided with a moisture barrier sealing system;
   an advancement mechanism for advancing a portion of the carrier from the compartment to within the chamber so that the powder associated with an advanced area of the carrier can be released from the carrier for inhalation by the patient through the patient port;
   wherein the moisture barrier sealing system is configured and arranged such that it is relaxable during advancement of the carrier, said sealing system being in sealing configuration prior to an advancement of the carrier, relaxed upon an advancement of the carrier and returned to its sealing configuration at the latest after release of the powder associated with said area of the carrier.

2. A device according to claim 1, wherein the compartment is provided within a cassette and said cassette is reversibly removable from the dry powder inhaler.

3. A device according to claim 2, wherein the cassette is a refill cassette.

4. A device according to claim 1, wherein said exit of the compartment is the only opening in the compartment; and/or wherein the compartment further houses a desiccator; and/or wherein part or all the interior portions of the walls of the compartment comprise a desiccant.

5. A device according to claim 1, wherein the moisture barrier sealing system comprises a seal.

6. A device according to claim 5, wherein the seal comprises a material having a Shore A durometer value equal to or less than 75 and/or wherein the seal comprises a material having a Shore A hardness value equal to or greater than 35; and/or wherein the seal comprises an elastomeric material selected from the group consisting of silicone rubber, EPDM, polypropylene blends, styrene-isoprene copolymers, combinations and mixtures thereof.

7. A device according to claim 1, wherein the moisture barrier sealing system is configured and arranged such that the sealing system is returned to its sealing configuration at least prior to release of the powder associated with said area of the carrier.

8. A device according to claim 7, wherein the device further comprises a clamping system, wherein said clamping system is configured and arranged such that it is moved into a clamping configuration at least prior to release of the powder associated with said area of the carrier and wherein said clamping system and said moisture barrier sealing system are configured and arranged relative to one another such that said area of the carrier will be clamped between the clamping system and the moisture barrier sealing system during release of the powder associated with said area of the carrier.

9. A device according to claim 8, wherein the clamping system is configured and arranged so that when the carrier is being advanced, the clamping system is out of its clamping configuration.

10. A device according to claim 1, wherein the moisture barrier sealing system is configured and arranged such that the sealing system is returned to its sealing configuration upon cessation of advancement of the carrier.

11. A device according to claim 1, wherein the moisture barrier sealing system comprises a seal coupled to a moveable member that is engaging a spring, said spring urging the moveable member in a first direction such that the moisture barrier seal seals the compartment exit, and wherein upon advancement of the carrier under the tension associated with the advancement of the carrier the moveable member moves in the opposite direction, so that the moisture barrier seal disengages, opening the compartment exit thereby allowing the carrier to advance through the exit, and wherein upon cessation of advancement of the carrier, the moveable member moves in its original direction under the force of the spring, so that the moisture barrier seal seals the compartment exit, in particular wherein said movement of said moveable member comprises a substantially rotational or linear movement.

12. A device according to claim 1, where the device further comprises a first clamping system and a second clamping system, wherein the first and second clamping systems are configured and arranged such that said first and second clamping systems are moved into a clamping configuration at least prior to release of the powder associated with said area of the carrier, so that said area of the carrier will be clamped between the first and the second clamping systems during release of the powder associated with said area of the carrier.

13. A device according to claim 12, wherein the clamping systems are configured and arranged so that when the carrier is being advanced, the clamping systems are out of their clamping configurations.

14. A device according to claim 1, wherein the elongate carrier is in the form of a tape or a web.

15. A device according to claim 1, wherein the elongate carrier is wound on a spool within said compartment, in particular a spool comprising an anti-unspooling mechanism, more particularly a spool comprising a friction brake.

16. A device according to claim 1, wherein the elongate carrier does not comprise a lid component.

17. A device for storing dry powder for use in a dry powder inhaler, said device provided in the form of a cassette comprising:
 a compartment housing an elongate carrier preloaded with a plurality of doses of finely divided powder comprising a biologically active substance, said powder being releasably retained on a surface of the carrier; said compartment being configured such that preloaded doses are sealed within said compartment and such that the carrier may be advanced from the compartment to the outside of the compartment through an exit provided with a moisture barrier sealing system,
 wherein said device is configured and arranged such that during use in a dry powder inhaler wherein a portion of the carrier is advanced so that the powder associated with an advanced area can be released from the carrier for inhalation by the patient through the patient port of the inhaler, the moisture barrier sealing system is relaxable during advancement of the carrier, so that said sealing system is in sealing configuration prior to an advancement of the carrier, will relax upon an advancement of the carrier and will be returned to its sealing configuration at the latest after release of the powder associated with said area of carrier.

18. A device according to claim 17, wherein the device is configured and arranged such that during use in a dry powder inhaler, the sealing system will be returned to its sealing configuration at least prior to release of the powder associated with said area of the carrier.

19. A device according to claim 18, wherein the device further comprises a clamping system, wherein the device is configured and arranged such that during use in a dry powder inhaler, the clamping system is movable, said clamping system being moved into a clamping configuration at least prior to release of the powder associated with said area of the carrier and such that said area of the carrier will be clamped between the clamping system and the moisture barrier sealing system during release of the powder associated with said area of the carrier.

20. A device according to claim 17, wherein the device is configured and arranged such that during use in a dry powder inhaler, the sealing system will be returned to its sealing configuration upon cessation of advancement of the carrier.

* * * * *